(12) United States Patent
Zhang et al.

(10) Patent No.: US 12,036,197 B2
(45) Date of Patent: Jul. 16, 2024

(54) COMPOSITION FOR IMPROVING BIOAVAILABILITY OF DRUGS

(71) Applicant: Jing Zhang, Jiangsu (CN)

(72) Inventors: Jing Zhang, Jiangsu (CN); Wenbo Jin, Jiangsu (CN)

(73) Assignee: Jing Zhang, Jiangsu (CN)

( * ) Notice: Subject to any disclaimer, the term of this patent is extended or adjusted under 35 U.S.C. 154(b) by 659 days.

(21) Appl. No.: 17/282,833

(22) PCT Filed: May 6, 2020

(86) PCT No.: PCT/CN2020/088646
§ 371 (c)(1),
(2) Date: Apr. 5, 2021

(87) PCT Pub. No.: WO2020/248742
PCT Pub. Date: Dec. 17, 2020

(65) Prior Publication Data
US 2021/0369660 A1 Dec. 2, 2021

(30) Foreign Application Priority Data

Jun. 10, 2019 (CN) .......................... 201910498795.6

(51) Int. Cl.
| | | |
|---|---|---|
| *A61K 31/198* | (2006.01) | |
| *A61K 31/194* | (2006.01) | |
| *A61K 47/20* | (2006.01) | |
| *A61K 47/32* | (2006.01) | |
| *A61K 47/36* | (2006.01) | |
| *A61P 43/00* | (2006.01) | |

(52) U.S. Cl.
CPC .......... *A61K 31/198* (2013.01); *A61K 31/194* (2013.01); *A61K 47/20* (2013.01); *A61K 47/32* (2013.01); *A61K 47/36* (2013.01); *A61P 43/00* (2018.01)

(58) Field of Classification Search
CPC .................................................. A61K 31/198
See application file for complete search history.

(56) References Cited

U.S. PATENT DOCUMENTS

| | | | |
|---|---|---|---|
| 2008/0241260 A1 | 10/2008 | Devarajan | |
| 2009/0280172 A1* | 11/2009 | Carreno-Gomez | ....... A61P 9/10 |
| | | | 514/616 |
| 2011/0142889 A1 | 6/2011 | Lee et al. | |

FOREIGN PATENT DOCUMENTS

| | | |
|---|---|---|
| CN | 1326784 A | 12/2001 |
| CN | 101518554 A | 9/2009 |
| CN | 101843595 A | 9/2010 |
| CN | 107320716 A | 11/2017 |
| CN | 108524866 A | 9/2018 |
| CN | 108653233 A | 10/2018 |
| CN | 10926024 A * | 1/2019 |
| CN | 101502540 A | 8/2019 |
| CN | 112057619 A | 12/2020 |
| KR | 20170115241 A | 10/2017 |
| WO | 2009008005 A1 | 1/2009 |
| WO | 2018098376 A1 | 5/2018 |

OTHER PUBLICATIONS

International Search Report in the international application No. PCT/CN2020/088646, mailed on Aug. 5, 2020.
Written Opinion of the International Searching Authority in the international application No. PCT/CN2020/088646, mailed on Aug. 5, 2020 and English translation provided by Google Translate.
International Preliminary Report on Patentability Chapter I from PCT/CN2020/088646 mailed on Dec. 23, 2021, and its English translation from WIPO.
Office action with search report from Chinese Patent Application No. 201910498795.6 dated Aug. 26, 2021, and its English translation from Global Dossier.
Research progress on oral route of insulin administration, Li Liu et al., Journal of modern food and pharmaceuticals, vol. 16, No. 6, 2007, pp. 62-65, Dec. 25, 2007, and its English translation generated from Google Translation.
Extended Supplementary Search Report from European Patent Application No. 20822549.0 dated Aug. 1, 2022.

* cited by examiner

*Primary Examiner* — Gina C Justice
(74) *Attorney, Agent, or Firm* — HAUPTMAN HAM, LLP

(57) ABSTRACT

A composition comprising: a surfactant, an acrylic polymer, chitin or its derivatives, and a metal ion chelating agent. Studies have shown that the composition can promote absorption of effective ingredients in the small intestine and improve their bioavailability.

12 Claims, 3 Drawing Sheets

COMPOSITION FOR IMPROVING BIOAVAILABILITY OF DRUGS

CROSS-REFERENCE TO RELATED APPLICATIONS

The present application is the U.S. national phase of PCT Application No. PCT/CN2020/088646 filed on May 6, 2020, which claims a priority to the Chinese patent application No. 201910498795.6 filed on Jun. 10, 2019, the disclosures of which are incorporated herein by reference in their entireties.

TECHNICAL FIELD

The invention relates to the technical field of biopharmaceutics, and specifically relates to a composition containing a surfactant, an acrylic polymer, chitin or its derivatives, and a metal ion chelating agent.

BACKGROUND ART

The technology of making drugs orally available has always been a research hotspot. This technology relates to realizing oral administration of enteric capsules of a drug substance that is conventionally administered via subcutaneous or intravenous injection only, such that the drug is delivered to the small intestine where it disintegrates, and is absorbed through the small intestine into the blood circulation with the assistance of a combination of different formulants.

In comparison with drugs for subcutaneous or intravenous administration, drugs for oral administration have two advantages: for patients, the drugs can be self-administered, are more acceptable, and pose a lower risk of infection; and for drug manufacturers, the drugs set out more lenient requirements on workshop conditions and allow reduced production costs.

However, there are also many obstacles and bottlenecks encountered in this field, such as how to prevent drugs from being degraded by various digestive enzymes in the intestinal microenvironment, how to promote smooth passage of drugs through small-intestinal villous epithelial cells, and how to minimize the side effects of orally administered formulations.

Orally administered drugs enter the blood circulation mainly through the carrier transport, pinocytosis, or the paracellular pathway. The influencing factors include the relative molecular mass, spatial structure and hydrophobicity of the drugs, as well as various barriers in the body, such as the acid barrier, enzymatic barrier and membrane barrier. In addition, the first pass effect after the drugs enter the portal venous system through the gastrointestinal tract and enter the liver is also a problem that must be addressed to make drugs available for oral administration.

So far, in studies for orally available polypeptide drugs, the strategies to improve absorption of orally administered drugs mainly include chemical modification, addition of absorption enhancers, addition of enzyme inhibitors, nano-carriers, liposome carriers, and micro-emulsion carriers.

SUMMARY OF INVENTION

For the above reasons, the applicant conducted extensive creative studies and discovered a novel composition prepared from a surfactant, an acrylic polymer, chitin or its derivatives, and a metal ion chelating agent. Studies have demonstrated that the composition according to the present invention can be prepared into a composite adjuvant which can, after combined with pharmaceutically active ingredients, improve absorption of the active ingredients in the small intestine. The composition according to the present invention is an organic whole that synergistically ensures absorption of a drug (effective ingredients or active ingredients) in the intestine.

The present invention is achieved through the following technical solutions.

Provided is a composition, comprising: a surfactant, an acrylic polymer, chitin or its derivatives, and a metal ion chelating agent.

Further provided is a pharmaceutical composition, comprising: a surfactant, an acrylic polymer, chitin or its derivatives, and a metal ion chelating agent.

The surfactant may be one or more of anionic surfactants or nonionic surfactants.

The acrylic polymer may be one or more of carbomer, carbomer 910, acrylic carbomer 934, and carbomer 934P.

The chitin or its derivatives may be one or more of chitin, chitosan, carboxymethyl chitosan, acylated chitosan, alkylated chitosan, hydroxylated chitosan, quaternary ammonium chitosan, chitosan oligosaccharide, and chitosan sulfate.

The metal ion chelating agent may be one or more of citric acid and/or its salt, tartaric acid and/or its salt, malic acid and/or its salt, maleic acid and/or its salt, gluconic acid and/or its salt, ethylenediaminetetraacetic acid and/or its salt, aminotriacetic acid and/or its salt, and diethylenetriaminepentaacetic acid and/or its salt.

In a preferred composition, the surfactant is sodium lauryl sulfate, the acrylic polymer is carbomer, the chitin or its derivatives are chitosan, and the metal ion chelating agent is sodium citrate.

The composition may be used to ensure absorption of drugs (effective ingredients or active ingredients) in the small intestine.

The composition may be used to promote absorption of drugs (effective ingredients or active ingredients) in the small intestine.

The surfactant, the acrylic polymer, the chitin or its derivatives, and the metal ion chelating agent may be in a weight ratio of 15-25:5-8:5-8:50-80.

Preferably, the surfactant, the acrylic polymer, the chitin or its derivatives, and the metal ion chelating agent may be in a weight ratio of 19-21:6-7:6-7:60-70.

The drugs (effective ingredients or active ingredients) may include, but are not limited to, polypeptides. The polypeptides include Exenatide, Nesiritide, Gonadorelin, Leuprolide, recombinant Glucagon, Oxytocin, Bivalirudin, Sermorelin, Gramicidin D, recombinant Insulin, Vasopressin, Cosyntropin, Octreotide, Vapreotide, Mecasermin, Teriparatide, ACTH, Pramlintide, Abaloparatide, rhGH, thymosin alpha-1, and the like.

The drugs (effective ingredients or active ingredients) may include, but are not limited to, insulin and its analogs.

The drugs (effective ingredients or active ingredients) may include, but are not limited to, growth hormone and its analogs.

Also provided is a composition promoting intestinal absorption, which is prepared from raw materials comprising a surfactant, an acrylic polymer, chitin or its derivatives, and a metal ion chelating agent.

The composition promoting intestinal absorption described above may be prepared into an adjuvant for use in an oral formulation.

The composition according to the present invention may be prepared as a novel adjuvant that enables oral administration of drugs (effective ingredients or active ingredients) which were previously for injection only and not for oral administration, thereby changing the administration route of the drugs (effective ingredients or active ingredients).

The composition according to the present invention can ensure intestinal absorption of drugs (effective ingredients or active ingredients) that are easily decomposed in the gastrointestinal tract.

The composition according to the present invention can promote intestinal absorption of drugs (effective ingredients or active ingredients) that are not easily absorbed in the gastrointestinal tract.

Since the composition according to the present invention promotes small-intestinal absorption which requires release of drugs in the small intestine to perform its functions, in pharmacodynamic and pharmacokinetic tests, drugs were administered to rodents by a small-intestinal catheter, or to mammals orally in the form of enteric capsules.

In the present invention, the composition was combined with each of the aforementioned polypeptides and tested for bioavailability in rodents, and meanwhile some polypeptides were selected for pharmacodynamic and pharmacokinetic tests on different animals.

DETAILED DESCRIPTION OF INVENTION

The following specific examples are given to illustrate technical solutions of the present invention, but the scope of protection of the present invention is not limited thereto.

The examples shown in this specification only exemplify the embodiments of the inventive concept. The scope of protection of the present invention should not be construed as limited to the specific forms described in the examples, but should also be extended to equivalent technical means conceivable by a person skilled in the art based on the idea of the present invention. Although some embodiments of the present invention are described below, the present invention is not limited to these embodiments or the field they are applied to. The following embodiments are merely illustrative, instructive, and not restrictive.

The following experiments according to the present invention are conclusive experiments conducted by the inventors based on many creative experiments, representing the technical solutions of the present invention to be claimed. The quantitative tests in the following Examples are all from triplicate experiments, and the data is given as the average or the average±standard deviation of the triplicate experiments.

Example 1. Significant Improvement in Efficacy of Exenatide (Exendin4, EXE4) after Small-Intestinal Administration The composition: sodium lauryl sulfate as the surfactant, carbomer as the acrylic polymer, chitosan as the chitin or its derivatives, and sodium citrate as the metal ion chelating agent, in a weight ratio of 20:6.5:6.5:65.

Exenatide and the above composition were mixed thoroughly in a weight ratio of 1:5, and reserved for further use.

Laboratory animals: SD male rats, intraperitoneally injected with 45 mg/kg STZ to establish a hyperglycemia model.

Small intestine efficacy test: administration was through subcutaneous injection (sc) or a small-intestine catheter (ei), and blood samples were collected at 0 h, 3 h, 6 h and 9 h to measure the blood sugar.

Figure 1:
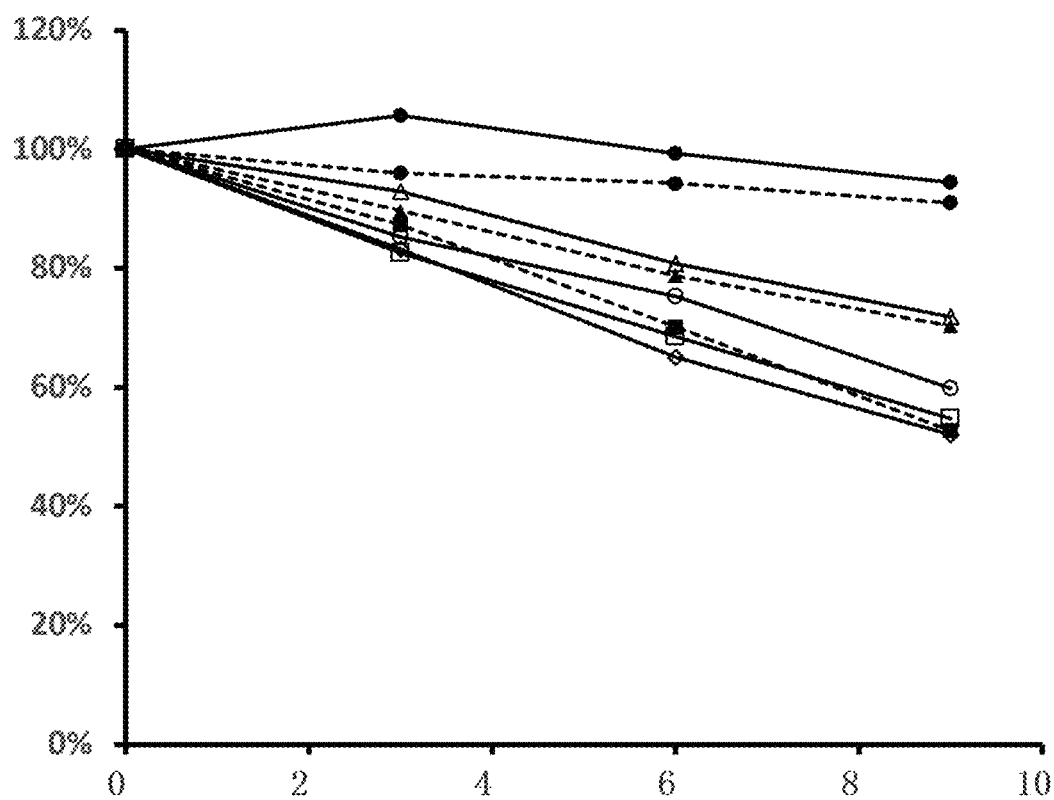
FIG. 1 shows the PD test with Exenatide in STZ rats, wherein the x axis is time (h), and the y axis is the hypoglycemic efficiency (%);
  the solid circles with a solid line represent small-intestinal injection of normal saline at 2 ml/kg,
  the solid squares with a dashed line represent subcutaneous injection of Exenatide at 1 µg/kg,
  the solid circles with a dashed line represent subcutaneous injection of Exenatide at 250 µg/kg,
  the solid triangles with a dashed line represent subcutaneous injection of Exenatide at 1 mg/kg,
  the hollow triangles with a solid line represent small-intestinal administration of the composition of Example 1+Exenatide (dose: Exenatide 30 µg/kg),
  the hollow circles with a solid line represent small-intestinal administration of the composition of Example 1+Exenatide (dose: Exenatide 40 µg/kg),
  the hollow squares with a solid line represent small-intestinal administration of the composition of Example 1+Exenatide (dose: Exenatide 50 µg/kg), and
  the hollow rhombuses with a solid line represent small-intestinal administration of the composition of Example 1+Exenatide (dose: Exenatide 60 µg/kg).

The results show that, in the absence of the composition described above, Exenatide after small-intestine administration showed a very weak hypoglycemic effect. When its dose reached 1 mg/kg, the hypoglycemic efficiency after 9 h was merely about 70%, far lower than the hypoglycemic efficiency of about 50% achieved by its subcutaneous dose of 1 µg/kg. However, after addition of the composition of the present invention, a dose of 50 µg/kg can achieve the hypoglycemic effect achieved by a subcutaneous dose of 1 µg/kg. See FIG. 1.

Example 2. Significant Improvement in Bioavailability of Exenatide after Small-Intestinal Administration Exenatide and the composition of Example 1 were mixed thoroughly in a weight ratio of 1:5, and reserved for further use.

Laboratory animals: adult male SD rats.

PK test for small-intestinal administration: Exenatide was administered to fasted adult SD rats in a volume of 1 ml/kg via a small-intestine catheter, such that the dose of Exenatide was 200 μg/kg. In another group, Exenatide at 200 μg/kg together with the composition of Example 1 of the present invention was administered via a small-intestine catheter (ei), and blood samples were collected from tail vein at 0 h, 0.5 h, 1 h, 1.5 h, 2 h, 2.5 h and 3 h after administration. The blood samples were anticoagulated with 10 mM EDTA and centrifuged at 4° C. at 3000 rpm for 5 min. The plasma was collected and subjected to quick freezing.

In order to avoid hypoglycemia in the animals, 1 g/kg glucose was given before administration.

ELISA assay: Coating with a mouse monoclonal antibody against the target polypeptide, blocking with 1% BSA, incubating with a blood sample or a standard diluted with 0.1% BSA, capturing with Biotin-labeled rabbit polyclonal antibody against the target polypeptide, incubating with HRP-conjugated strepavidin, then developing with TMB, which was stopped with HCl, and reading at 450 nm. A standard curve was obtained from standards, and the concentration of the target polypeptide in the plasma was calculated.

AUC was calculated based on the PK curve, and the bioavailability of small-intestinal administration was calculated with respect to 100% of the bioavailability of intravenous injection (iv).

Figure 2:
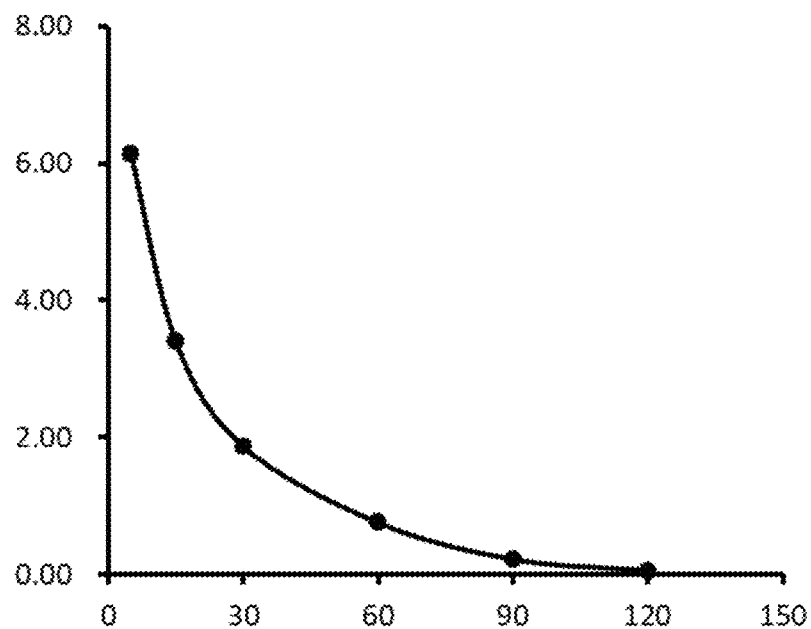
FIG. 2 shows the iv PK test with Exenatide in rats; wherein the x axis is time (h), and the y axis is the plasma concentration of Exenatide in rats (ng/ml).
Figure 3:
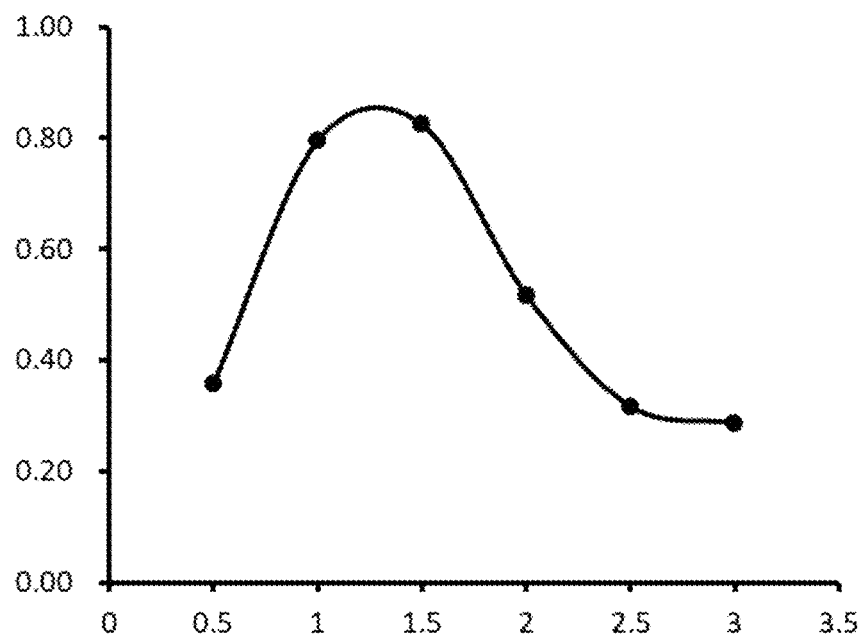
FIG. 3 shows the ei PK test with Exenatide/the composition of Example 1 in rats; wherein the x axis is time (h), and the y axis is the plasma concentration of Exenatide in rats (ng/ml).

The results showed that the AUC in the PK curve for 1 μg/kg i.v. injected Exenatide was 0.93 ng/ml·h, while the blood concentration after the small-intestinal injection of 200 μg/kg was lower than the detection limit of ELISA. After addition of the composition of Example 1, the AUC in the PK curve could reach 1.47 ng/ml·h, and the bioavailability of small-intestinal administration was about 0.79%. The test results are shown in FIG. 2 and FIG. 3.

Example 3. Significant Improvement in Oral Bioavailability of Exenatide 0.7 mg of Exenatide was mixed thoroughly with 200 mg of the composition of Example 1, freeze-dried, loaded into a #3 enteric capsule, and reserved for further use;

0.7 mg of Exenatide was mixed thoroughly with 400 mg of the composition of Example 1, freeze-dried, loaded into a #0 enteric capsule, and reserved for further use;

0.7 mg of Exenatide was mixed thoroughly with 600 mg of the composition of Example 1, freeze-dried, loaded into a #00 enteric capsule, and reserved for further use;

0.7 mg of Exenatide was mixed thoroughly with 200 mg of the composition of Example 1, freeze-dried, loaded into a #3 normal capsule, and reserved for further use;

0.7 mg of Exenatide was mixed thoroughly with 200 mg of mannitol, freeze-dried, loaded into a #3 enteric capsule, and reserved for further use.

Laboratory Animals: Adult Male Beagle Dogs.

PK test for oral administration: The enteric capsules were orally administered to fasted animals, and then blood samples were collected after 0.5, 1, 1.5, 2, 2.5, and 3 h. The blood samples were anticoagulated with 10 mM EDTA, and centrifuged at 4° C. at 3000 rpm for 5 min. Plasma was collected and subjected to quick freezing.

Figure 4:
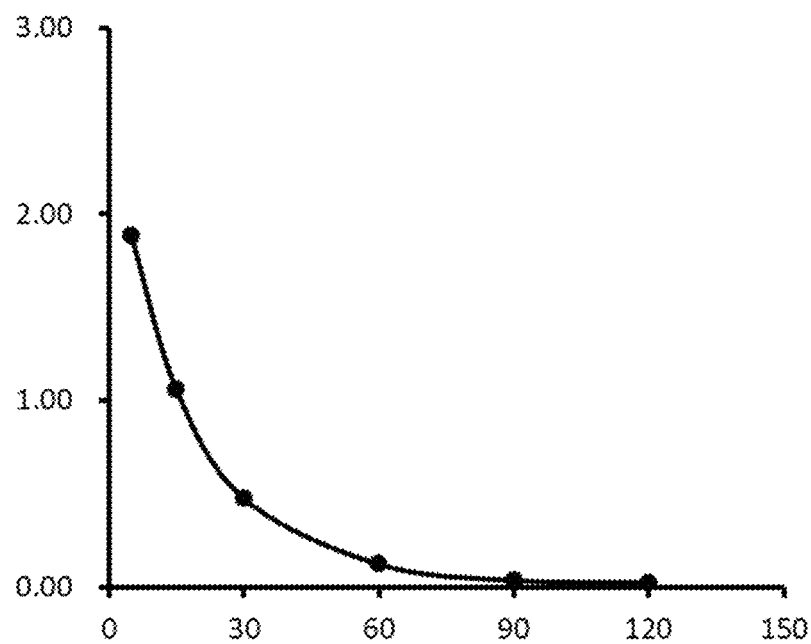
FIG. 4 shows the iv PK test with Exenatide in beagle dogs; wherein the x axis is time (h), and the y axis is the plasma concentration of Exenatide in beagle dogs (ng/ml).
Figure 5:
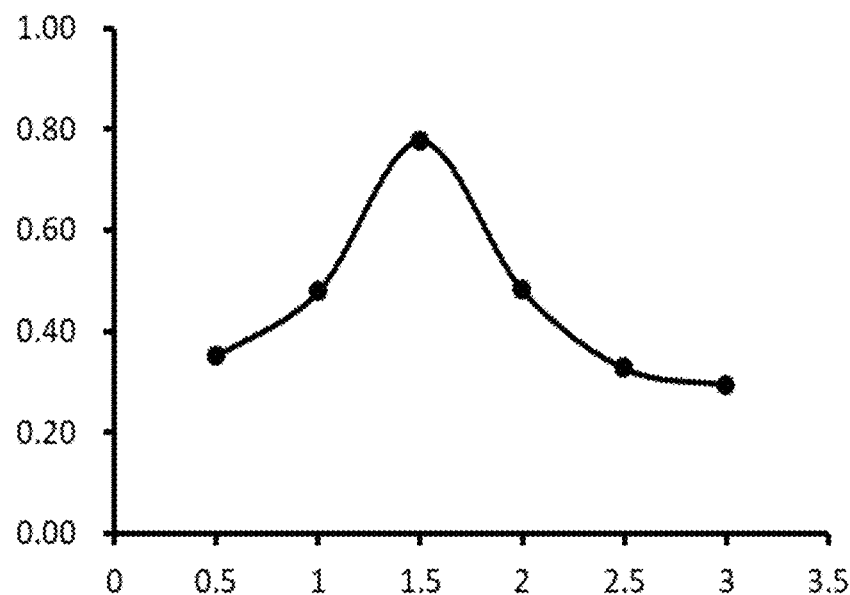
FIG. 5 shows the po PK test with Exenatide/the composition of Example 1 in beagle dogs; wherein the x axis is time (h), and the y axis is the plasma concentration of Exenatide in beagle dogs (ng/ml).

PK test for intravenous administration: Exenatide was injected intravenously to fasted animals at 0.3 μg/kg, and then blood samples were collected after 5, 15, 30, 60, 90, and 120 min. The blood samples were anticoagulated with 10 mM EDTA, and centrifuged at 4° C. at 3000 rpm for 5 min. Plasma was collected and subjected to quick freezing. See FIG. 4 and FIG. 5.

In order to avoid hypoglycemia in animals, 1 g/kg glucose was given before administration.

ELISA assay: Coating with a mouse monoclonal antibody against the target polypeptide, blocking with 1% BSA, incubating with a blood sample or a standard diluted with 0.1% BSA, capturing with Biotin-labeled rabbit polyclonal antibody against the target polypeptide, incubating with HRP-conjugated strepavidin, then developing with TMB, which was stopped with HCl, and reading at 450 nm. A standard curve was obtained from standards, and the concentration of the target polypeptide in the plasma was calculated.

AUC was calculated based on the PK curve, and the bioavailability of small-intestinal administration was calculated with respect to 100% of the bioavailability of intravenous injection (iv).

The PK data for beagle dogs show that the AUC of 0.3 μg/kg intravenously injected Exenatide was about 0.82 ng/ml·h, and the AUC of 0.7 mg orally administered Exenatide/the composition of Example 1 was about 1.36 ng/ml·h. The bioavailability of orally administered Exenatide/Composition of Example 1 was about 0.83%.

Without the assistance of the composition of the present invention, Exenatide cannot successfully enter the blood. After addition of the composition of the present invention, the efficiency of entering the blood was significantly improved. As the weight of the composition of Example 1 increased, the efficiency of Exenatide entering the blood also slightly increased, but to a limited degree. Considering convenience of oral administration and effectiveness of drugs, the dose of #3 capsules was more appropriate.

TABLE 1 po PD tests on beagle dogs with Exenatide/Composition of Example 1

| Drug | Adjuvant | Capsules | 0.5 h | 1.0 h | 1.5 h | 2.0 h | 2.5 h | 3.0 h | AUC ng/ml · h |
|---|---|---|---|---|---|---|---|---|---|
| Exenatide 0.7 mg | Composition of Example 1 200 mg | #3 Enteric | 0.350 | 0.479 | 0.777 | 0.482 | 0.326 | 0.294 | 1.281 |
| Exenatide 0.7 mg | Composition of Example 1 400 mg | #0 Enteric | 0.319 | 0.442 | 0.814 | 0.482 | 0.290 | 0.268 | 1.240 |
| Exenatide 0.7 mg | Composition of Example 1 600 mg | #00 Enteric | 0.364 | 0.549 | 0.893 | 0.510 | 0.380 | 0.313 | 1.426 |

TABLE 1-continued po PD tests on beagle dogs with Exenatide/Composition of Example 1

| Drug | Adjuvant | Capsules | 0.5 h | 1.0 h | 1.5 h | 2.0 h | 2.5 h | 3.0 h | AUC ng/ml · h |
|---|---|---|---|---|---|---|---|---|---|
| Exenatide 0.7 mg | Composition of Example 1 200 mg | #3 Normal | (0.032) | 0.013 | (0.055) | 0.024 | (0.026) | (0.021) | — |
| Exenatide 0.7 mg | Mannitol 200 mg | #3 Enteric | (0.026) | (0.021) | 0.007 | (0.049) | (0.132) | (0.037) | — |

Example 4. Exenatide/Composition of Example 1 can Significantly Inhibit the Increase in Postprandial Blood Sugar of Alloxan Beagle Dogs 0.7 mg of Exenatide was mixed thoroughly with 200 mg of the composition of Example 1, freeze-dried, loaded into a #3 enteric capsule, and reserved for further use.

Laboratory Animals: Adult Male Beagle Dogs.

Physical examination and adaptation of animals: Blood samples from fasted animals were collected to test blood biochemical indicators. Once everything was confirmed normal, the animals were placed in a quiet room to adapt for 1 week. The daily feeding time and feeding amount were required to be consistent.

Data collection before modeling: Blood samples were collected at 4 time points every day (before feeding, and 2 h, 4 h, 6 h after feeding) for 5 consecutive days.

Modeling: an Alloxan solution was intravenously injected at 60 mg/kg to fasted animals. One week later, blood samples were collected at 4 time points every day (before feeding, and 2 h, 4 h, 6 h after feeding) for 5 consecutive days. Qualification of the model was evaluated based on the collected data. If the model was qualified, the efficacy test was started.

Efficacy test: Animals swallowed the test capsules before feeding, and blood samples were collected at 4 time points (before feeding, and 2 h, 4 h, 6 h after feeding).

Figure 6:
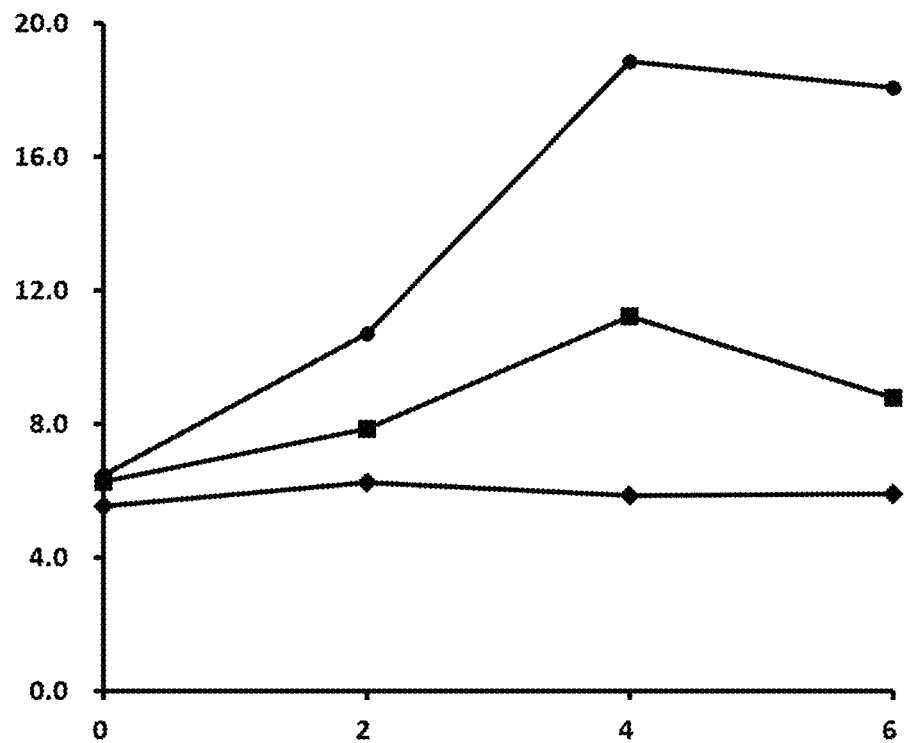
FIG. 6 shows the PD test with Exenatide in Alloxan beagle dogs; wherein the x axis is time (h), and the y axis is the blood sugar (mM) in beagle dogs;
  the solid circles with a solid line are the postprandial blood sugar of Alloxan beagle dogs, the solid squares with a solid line are the postprandial blood sugar of Alloxan beagle dogs after swallowing Exenatide/the composition of Example 1, and the solid rhombuses with a solid line are the postprandial blood sugar of normal beagle dogs.

The results show that the Exenatide/the composition of Example 1 can significantly inhibit the increase in postprandial blood sugar of Alloxan-modelled beagle dogs. See FIG. 6.

Example 5. The Composition of the Present Invention Significantly Improves the Bioavailability of Nesiritide after Small-Intestinal Administration The composition of the present invention: Tween 80, carbomer 910, carboxymethyl chitosan, and sodium tartrate, in a weight ratio of 3:1:1:10.

Nesiritide and the above composition were mixed thoroughly in a weight ratio of 1:5, and reserved for further use.

Laboratory Animals: Adult Male SD Rats.

PK test for small-intestinal administration: Nesiritide was administered to fasted adult SD rats in a volume of 1 ml/kg via a small-intestine catheter, such that the dose of Nesiritide was 200 μg/kg. In another group, Nesiritide at 200 μg/kg together with the above composition was injected via a small-intestine catheter (ei), and blood samples were collected from tail vein at 0 h, 0.5 h, 1 h, 1.5 h, 2 h, 2.5 h and 3 h after administration. The blood samples were anticoagulated with 10 mM EDTA and centrifuged at 4° C. at 3000 rpm for 5 min. The plasma was collected and subjected to quick freezing.

PK test for intravenous administration: Nesiritide was intravenously injected to fasted animals at 1 μg/kg, and blood samples were collected at 5, 15, 30, 60, 90 and 120 min. The blood samples were anticoagulated with 10 mM EDTA and centrifuged at 4° C. at 3000 rpm for 5 min. The plasma was collected and subjected to quick freezing.

ELISA assay: Coating with a mouse monoclonal antibody against the target polypeptide, blocking with 1% BSA, incubating with a blood sample or a standard diluted with 0.1% BSA, capturing with Biotin-labeled rabbit polyclonal antibody against the target polypeptide, incubating with HRP-conjugated strepavidin, then developing with TMB, which was stopped with HCl, and reading at 450 nm. A standard curve was obtained from standards, and the concentration of the target polypeptide in the plasma was calculated.

AUC was calculated based on the PK curve, and the bioavailability of small-intestinal administration was calculated with respect to 100% of the bioavailability of intravenous injection (iv).

The results showed that the blood concentration of Nesiritide after the small-intestinal administration at 200 μg/kg was lower than the detection limit of ELISA. After addition of the above composition, the bioavailability of small-intestinal administration could reach 1.22%.

Example 6. Significant Improvement in Bioavailability of Gonadorelin after Small-Intestinal Administration The composition of the present invention: sodium taurocholate, carbomer 934P, alkylated chitosan, and sodium maleate, in a weight ratio of 17:6:6.5:55.

Gonadorelin and the above composition were mixed thoroughly in a weight ratio of 1:5, and reserved for further use.

Laboratory Animals: Adult Male SD Rats.

PK test for small-intestinal administration: Gonadorelin was administered to fasted adult SD rats in a volume of 1 ml/kg via a small-intestine catheter, such that the dose of Gonadorelin was 200 μg/kg. In another group, Gonadorelin at 200 μg/kg together with the composition of the present invention was injected via a small-intestine catheter (ei), and blood samples were collected from tail vein at 0 h, 0.5 h, 1 h, 1.5 h, 2 h, 2.5 h and 3 h after administration. The blood samples were anticoagulated with 10 mM EDTA and centrifuged at 4° C. at 3000 rpm for 5 min. The plasma was collected and subjected to quick freezing.

PK test for intravenous administration: Gonadorelin was intravenously injected to fasted animals at 1 μg/kg, and blood samples were collected at 5, 15, 30, 60, 90 and 120 min. The blood samples were anticoagulated with 10 mM EDTA and centrifuged at 4° C. at 3000 rpm for 5 min. The plasma was collected and subjected to quick freezing.

ELISA assay: Coating with a mouse monoclonal antibody against the target polypeptide, blocking with 1% BSA, incubating with a blood sample or a standard diluted with 0.1% BSA, capturing with Biotin-labeled rabbit polyclonal antibody against the target polypeptide, incubating with HRP-conjugated strepavidin, then developing with TMB, which was stopped with HCl, and reading at 450 nm. A standard curve was obtained from standards, and the concentration of the target polypeptide in the plasma was calculated.

AUC was calculated based on the PK curve, and the bioavailability of small-intestinal administration was calculated with respect to 100% of the bioavailability of intravenous injection (iv).

The results showed that the blood concentration of Gonadorelin after the small-intestinal administration at 200 μg/kg was lower than the detection limit of ELISA. After addition of the composition of the present invention, the bioavailability of small-intestinal administration could reach 1.58%.

Example 7. The Composition of the Present Invention Significantly Improves Bioavailability of Leuprolide after Small-Intestinal Administration The composition of the present invention: polyethylene glycol 4000, carbomer, chitosan oligosaccharide, and citric acid, in a weight ratio of 19:6:6:60.

Leuprolide and the composition of the present invention were mixed thoroughly in a weight ratio of 1:5, and reserved for further use.

Laboratory Animals: Adult Male SD Rats.

PK test for small-intestinal administration: Leuprolide was administered to fasted adult SD rats in a volume of 1 ml/kg via a small-intestine catheter, such that the dose of Leuprolide was 200 μg/kg. In another group, Leuprolide at 200 μg/kg together with the composition of the present invention was injected via a small-intestine catheter (ei), and blood samples were collected from tail vein at 0 h, 0.5 h, 1 h, 1.5 h, 2 h, 2.5 h and 3 h after administration. The blood samples were anticoagulated with 10 mM EDTA and centrifuged at 4° C. at 3000 rpm for 5 min. The plasma was collected and subjected to quick freezing.

PK test for intravenous administration: Leuprolide was intravenously injected to fasted animals at 1 μg/kg, and blood samples were collected at 5, 15, 30, 60, 90 and 120 min. The blood samples were anticoagulated with 10 mM EDTA and centrifuged at 4° C. at 3000 rpm for 5 min. The plasma was collected and subjected to quick freezing.

ELISA assay: Coating with a mouse monoclonal antibody against the target polypeptide, blocking with 1% BSA, incubating with a blood sample or a standard diluted with 0.1% BSA, capturing with Biotin-labeled rabbit polyclonal antibody against the target polypeptide, incubating with HRP-conjugated strepavidin, then developing with TMB, which was stopped with HCl, and reading at 450 nm. A standard curve was obtained from standards, and the concentration of the target polypeptide in the plasma was calculated.

AUC was calculated based on the PK curve, and the bioavailability of small-intestinal administration was calculated with respect to 100% of the bioavailability of intravenous injection (iv).

The results showed that the blood concentration of Leuprolide after the small-intestinal administration at 200 μg/kg was lower than the detection limit of ELISA. After addition of the composition of the present invention, the bioavailability of small-intestinal administration could reach 1.32%.

Example 8. The Composition of the Present Invention Significantly Improves Bioavailability of Teduglutide after Small-Intestinal Administration The composition of the present invention: Tween 80, Carbomer 910, carboxymethyl Chitosan, and Sodium Tartrate, in a weight ratio of 25:8:8:80.

Teduglutide and the composition of the present invention were mixed thoroughly in a weight ratio of 1:5, and reserved for further use.

Laboratory Animals: Adult Male SD Rats.

PK test for small-intestinal administration: Teduglutide was administered to fasted adult SD rats in a volume of 1 ml/kg via a small-intestine catheter, such that the dose of Teduglutide was 200 μg/kg. In another group, Teduglutide at 200 μg/kg together with the composition of the present invention was injected via a small-intestine catheter (ei), and blood samples were collected from tail vein at 0 h, 0.5 h, 1 h, 1.5 h, 2 h, 2.5 h and 3 h after administration. The blood samples were anticoagulated with 10 mM EDTA and centrifuged at 4° C. at 3000 rpm for 5 min. The plasma was collected and subjected to quick freezing.

PK test for intravenous administration: Teduglutide was intravenously injected to fasted animals at 1 μg/kg, and blood samples were collected at 5, 15, 30, 60, 90 and 120 min. The blood samples were anticoagulated with 10 mM EDTA and centrifuged at 4° C. at 3000 rpm for 5 min. The plasma was collected and subjected to quick freezing.

ELISA assay: Coating with a mouse monoclonal antibody against the target polypeptide, blocking with 1% BSA, incubating with a blood sample or a standard diluted with 0.1% BSA, capturing with Biotin-labeled rabbit polyclonal antibody against the target polypeptide, incubating with HRP-conjugated strepavidin, then developing with TMB, which was stopped with HCl, and reading at 450 nm. A standard curve was obtained from standards, and the concentration of the target polypeptide in the plasma was calculated.

AUC was calculated based on the PK curve, and the bioavailability of small-intestinal administration was calculated with respect to 100% of the bioavailability of intravenous injection (iv).

The results showed that the blood concentration of Teduglutide after the small-intestinal administration at 200 μg/kg was lower than the detection limit of ELISA. After addition of the composition of the present invention, the bioavailability of small-intestinal administration could reach 2.13%.

Example 9. The Composition of the Present Invention Significantly Improves Bioavailability of Oxytocin after Small-Intestinal Administration The composition of the present invention: sodium lauryl sulfate, carbomer 934, water-soluble chitosan, disodium edetate, in a weight ratio of 24:7.5:7:75.

Oxytocin and the composition of the present invention were mixed thoroughly in a weight ratio of 1:5, and reserved for further use.

Laboratory Animals: Adult Male SD Rats.

PK test for small-intestinal administration: Oxytocin was administered to fasted adult SD rats in a volume of 1 ml/kg via a small-intestine catheter, such that the dose of Oxytocin was 200 μg/kg. In another group, Oxytocin at 200 μg/kg together with the composition of the present invention was injected via a small-intestine catheter (ei), and blood samples were collected from tail vein at 0 h, 0.5 h, 1 h, 1.5 h, 2 h, 2.5 h and 3 h after administration. The blood samples were anticoagulated with 10 mM EDTA and centrifuged at 4° C. at 3000 rpm for 5 min. The plasma was collected and subjected to quick freezing.

PK test for intravenous administration: Oxytocin was intravenously injected to fasted animals at 1 μg/kg, and blood samples were collected at 5, 15, 30, 60, 90 and 120 min. The blood samples were anticoagulated with 10 mM EDTA and centrifuged at 4° C. at 3000 rpm for 5 min. The plasma was collected and subjected to quick freezing.

ELISA assay: Coating with a mouse monoclonal antibody against the target polypeptide, blocking with 1% BSA, incubating with a blood sample or a standard diluted with 0.1% BSA, capturing with Biotin-labeled rabbit polyclonal antibody against the target polypeptide, incubating with HRP-conjugated strepavidin, then developing with TMB, which was stopped with HCl, and reading at 450 nm. A standard curve was obtained from standards, and the concentration of the target polypeptide in the plasma was calculated.

AUC was calculated based on the PK curve, and the bioavailability of small-intestinal administration was calculated with respect to 100% of the bioavailability of intravenous injection (iv).

The results showed that the blood concentration of Oxytocin after the small-intestinal administration at 200 μg/kg was lower than the detection limit of ELISA. After addition of the composition of the present invention, the bioavailability of small-intestinal administration could reach 2.58%.

Example 10. The Composition of the Present Invention Significantly Improves Bioavailability of Bivalirudin after Small-Intestinal Administration The composition of the present invention: sodium lauryl sulfate, carbomer, chitosan, and citric acid, in a weight ratio of 19:6.5:7:67.

Bivalirudin and the composition of the present invention were mixed thoroughly in a weight ratio of 1:5, and reserved for further use.

Laboratory Animals: Adult Male SD Rats.

PK test for small-intestinal administration: Bivalirudin was administered to fasted adult SD rats in a volume of 1 ml/kg via a small-intestine catheter, such that the dose of Bivalirudin was 200 μg/kg. In another group, Bivalirudin at 200 μg/kg together with the composition of the present invention was injected via a small-intestine catheter (ei), and blood samples were collected from tail vein at 0 h, 0.5 h, 1 h, 1.5 h, 2 h, 2.5 h and 3 h after administration. The blood samples were anticoagulated with 10 mM EDTA and centrifuged at 4° C. at 3000 rpm for 5 min. The plasma was collected and subjected to quick freezing.

PK test for intravenous administration: Bivalirudin was intravenously injected to fasted animals at 1 μg/kg, and blood samples were collected at 5, 15, 30, 60, 90 and 120 min. The blood samples were anticoagulated with 10 mM EDTA and centrifuged at 4° C. at 3000 rpm for 5 min. The plasma was collected and subjected to quick freezing.

ELISA assay: Coating with a mouse monoclonal antibody against the target polypeptide, blocking with 1% BSA, incubating with a blood sample or a standard diluted with 0.1% BSA, capturing with Biotin-labeled rabbit polyclonal antibody against the target polypeptide, incubating with HRP-conjugated strepavidin, then developing with TMB, which was stopped with HCl, and reading at 450 nm. A standard curve was obtained from standards, and the concentration of the target polypeptide in the plasma was calculated.

AUC was calculated based on the PK curve, and the bioavailability of small-intestinal administration was calculated with respect to 100% of the bioavailability of intravenous injection (iv).

The results showed that the blood concentration of Bivalirudin after the small-intestinal administration at 200 μg/kg was lower than the detection limit of ELISA. After addition of the composition of the present invention, the bioavailability of small-intestinal administration could reach 1.63%.

Example 11. The Composition of the Present Invention Significantly Improves Bioavailability of Sermorelin after Small-Intestinal Administration The composition of the present invention: sodium lauryl sulfate, carbomer, chitosan, and sodium citrate, in a weight ratio of 3:1:1:10.

Sermorelin and the composition of the present invention were mixed thoroughly in a weight ratio of 1:5, and reserved for further use.

Laboratory Animals: Adult Male SD Rats.

PK test for small-intestinal administration: Sermorelin was administered to fasted adult SD rats in a volume of 1 ml/kg via a small-intestine catheter, such that the dose of Sermorelin was 200 μg/kg. In another group, Sermorelin at 200 μg/kg together with the composition of the present invention was injected via a small-intestine catheter (ei), and blood samples were collected from tail vein at 0 h, 0.5 h, 1 h, 1.5 h, 2 h, 2.5 h and 3 h after administration. The blood samples were anticoagulated with 10 mM EDTA and centrifuged at 4° C. at 3000 rpm for 5 min. The plasma was collected and subjected to quick freezing.

PK test for intravenous administration: Sermorelin was intravenously injected to fasted animals at 1 μg/kg, and blood samples were collected at 5, 15, 30, 60, 90 and 120 min. The blood samples were anticoagulated with 10 mM EDTA and centrifuged at 4° C. at 3000 rpm for 5 min. The plasma was collected and subjected to quick freezing.

ELISA assay: Coating with a mouse monoclonal antibody against the target polypeptide, blocking with 1% BSA, incubating with a blood sample or a standard diluted with 0.1% BSA, capturing with Biotin-labeled rabbit polyclonal antibody against the target polypeptide, incubating with HRP-conjugated strepavidin, then developing with TMB, which was stopped with HCl, and reading at 450 nm. A standard curve was obtained from standards, and the concentration of the target polypeptide in the plasma was calculated.

AUC was calculated based on the PK curve, and the bioavailability of small-intestinal administration was calculated with respect to 100% of the bioavailability of intravenous injection (iv).

The results showed that the blood concentration of Sermorelin after the small-intestinal administration at 200 μg/kg was lower than the detection limit of ELISA. After addition of the composition of the present invention, the bioavailability of small-intestinal administration could reach 1.22%.

Example 12. The Composition of the Present Invention Significantly Improves Bioavailability of Gramicidin D after Small-Intestinal Administration The composition of the present invention: sodium lauryl sulfate, carbomer, chitosan, and sodium citrate, in a weight ratio of 19:6:6:60.

Gramicidin and the composition of the present invention were mixed thoroughly in a weight ratio of 1:5, and reserved for further use.

Laboratory Animals: Adult Male SD Rats.

PK test for small-intestinal administration: Gramicidin was administered to fasted adult SD rats in a volume of 1 ml/kg via a small-intestine catheter, such that the dose of Gramicidin was 200 μg/kg. In another group, Gramicidin at 200 μg/kg together with the composition of the present invention was injected via a small-intestine catheter (ei), and blood samples were collected from tail vein at 0 h, 0.5 h, 1 h, 1.5 h, 2 h, 2.5 h and 3 h after administration. The blood samples were anticoagulated with 10 mM EDTA and centrifuged at 4° C. at 3000 rpm for 5 min. The plasma was collected and subjected to quick freezing.

PK test for intravenous administration: Gramicidin was intravenously injected to fasted animals at 1 μg/kg, and blood samples were collected at 5, 15, 30, 60, 90 and 120 min. The blood samples were anticoagulated with 10 mM EDTA and centrifuged at 4° C. at 3000 rpm for 5 min. The plasma was collected and subjected to quick freezing.

ELISA assay: Coating with a mouse monoclonal antibody against the target polypeptide, blocking with 1% BSA, incubating with a blood sample or a standard diluted with 0.1% BSA, capturing with Biotin-labeled rabbit polyclonal antibody against the target polypeptide, incubating with HRP-conjugated strepavidin, then developing with TMB, which was stopped with HCl, and reading at 450 nm. A standard curve was obtained from standards, and the concentration of the target polypeptide in the plasma was calculated.

AUC was calculated based on the PK curve, and the bioavailability of small-intestinal administration was calculated with respect to 100% of the bioavailability of intravenous injection (iv).

The results showed that the blood concentration of Gramicidin after the small-intestinal administration at 200 μg/kg was lower than the detection limit of ELISA. After addition of the composition of the present invention, the bioavailability of small-intestinal administration could reach 1.18%.

Example 13. The Composition of the Present Invention Significantly Improves Bioavailability of Recombinant Insulin (rInsulin) after Small-Intestinal Administration The composition of the present invention: sodium lauryl sulfate, carbomer, chitosan, and sodium citrate, in a weight ratio of 20:6.5:6.5:68.

rInsulin and the composition of the present invention were mixed thoroughly in a weight ratio of 1:5, and reserved for further use.

Laboratory Animals: Adult Male SD Rats.

PK test for small-intestinal administration: rInsulin was administered to fasted adult SD rats in a volume of 1 ml/kg via a small-intestine catheter, such that the dose of rInsulin was 200 μg/kg. In another group, rInsulin at 200 μg/kg together with the composition of the present invention was injected via a small-intestine catheter (ei), and blood samples were collected from tail vein at 0 h, 0.5 h, 1 h, 1.5 h, 2 h, 2.5 h and 3 h after administration. The blood samples were anticoagulated with 10 mM EDTA and centrifuged at 4° C. at 3000 rpm for 5 min. The plasma was collected and subjected to quick freezing.

PK test for intravenous administration: rInsulin was intravenously injected to fasted animals at 1 μg/kg, and blood samples were collected at 5, 15, 30, 60, 90 and 120 min. The blood samples were anticoagulated with 10 mM EDTA and centrifuged at 4° C. at 3000 rpm for 5 min. The plasma was collected and subjected to quick freezing.

ELISA assay: Coating with a mouse monoclonal antibody against the target polypeptide, blocking with 1% BSA, incubating with a blood sample or a standard diluted with 0.1% BSA, capturing with Biotin-labeled rabbit polyclonal antibody against the target polypeptide, incubating with HRP-conjugated strepavidin, then developing with TMB, which was stopped with HCl, and reading at 450 nm. A standard curve was obtained from standards, and the concentration of the target polypeptide in the plasma was calculated.

AUC was calculated based on the PK curve, and the bioavailability of small-intestinal administration was calculated with respect to 100% of the bioavailability of intravenous injection (iv).

The results showed that the blood concentration of rInsulin after the small-intestinal administration at 200 μg/kg was lower than the detection limit of ELISA. After addition of the composition of the present invention, the bioavailability of small-intestinal administration could reach 0.89%.

Example 14. The Composition of the Present Invention Significantly Improves Bioavailability of Vasopressin after Small-Intestinal Administration The composition of the present invention: sodium lauryl sulfate, carbomer, chitosan, and sodium citrate, in a weight ratio of 23:8:7.5:80.

Vasopressin and the composition of the present invention were mixed thoroughly in a weight ratio of 1:5, and reserved for further use.

Laboratory Animals: Adult Male SD Rats.

PK test for small-intestinal administration: Vasopressin was administered to fasted adult SD rats in a volume of 1 ml/kg via a small-intestine catheter, such that the dose of Vasopressin was 200 μg/kg. In another group, Vasopressin at 200 μg/kg together with the composition of the present invention was injected via a small-intestine catheter (ei), and blood samples were collected from tail vein at 0 h, 0.5 h, 1 h, 1.5 h, 2 h, 2.5 h and 3 h after administration. The blood samples were anticoagulated with 10 mM EDTA and centrifuged at 4° C. at 3000 rpm for 5 min. The plasma was collected and subjected to quick freezing.

PK test for intravenous administration: Vasopressin was intravenously injected to fasted animals at 1 μg/kg, and blood samples were collected at 5, 15, 30, 60, 90 and 120 min. The blood samples were anticoagulated with 10 mM EDTA and centrifuged at 4° C. at 3000 rpm for 5 min. The plasma was collected and subjected to quick freezing.

ELISA assay: Coating with a mouse monoclonal antibody against the target polypeptide, blocking with 1% BSA, incubating with a blood sample or a standard diluted with 0.1% BSA, capturing with Biotin-labeled rabbit polyclonal antibody against the target polypeptide, incubating with HRP-conjugated strepavidin, then developing with TMB, which was stopped with HCl, and reading at 450 nm. A standard curve was obtained from standards, and the concentration of the target polypeptide in the plasma was calculated.

AUC was calculated based on the PK curve, and the bioavailability of small-intestinal administration was calculated with respect to 100% of the bioavailability of intravenous injection (iv).

The results showed that the blood concentration of Vasopressin after the small-intestinal administration at 200 μg/kg was lower than the detection limit of ELISA. After addition of the composition of the present invention, the bioavailability of small-intestinal administration could reach 1.81%.

Example 15. The Composition of the Present Invention Significantly Improves Bioavailability of Cosyntropin after Small-Intestinal Administration The composition of the present invention: sodium lauryl sulfate, carbomer, chitosan, and sodium citrate, in a weight ratio of 10:3:3:30.

Cosyntropin and the composition of the present invention were mixed thoroughly in a weight ratio of 1:5, and reserved for further use.

Laboratory Animals: Adult Male SD Rats.

PK test for small-intestinal administration: Cosyntropin was administered to fasted adult SD rats in a volume of 1 ml/kg via a small-intestine catheter, such that the dose of Cosyntropin was 200 µg/kg. In another group, Cosyntropin at 200 µg/kg together with the composition of the present invention was injected via a small-intestine catheter (ei), and blood samples were collected from tail vein at 0 h, 0.5 h, 1 h, 1.5 h, 2 h, 2.5 h and 3 h after administration. The blood samples were anticoagulated with 10 mM EDTA and centrifuged at 4° C. at 3000 rpm for 5 min. The plasma was collected and subjected to quick freezing.

PK test for intravenous administration: Cosyntropin was intravenously injected to fasted animals at 1 µg/kg, and blood samples were collected at 5, 15, 30, 60, 90 and 120 min. The blood samples were anticoagulated with 10 mM EDTA and centrifuged at 4° C. at 3000 rpm for 5 min. The plasma was collected and subjected to quick freezing.

ELISA assay: Coating with a mouse monoclonal antibody against the target polypeptide, blocking with 1% BSA, incubating with a blood sample or a standard diluted with 0.1% BSA, capturing with Biotin-labeled rabbit polyclonal antibody against the target polypeptide, incubating with HRP-conjugated strepavidin, then developing with TMB, which was stopped with HCl, and reading at 450 nm. A standard curve was obtained from standards, and the concentration of the target polypeptide in the plasma was calculated.

AUC was calculated based on the PK curve, and the bioavailability of small-intestinal administration was calculated with respect to 100% of the bioavailability of intravenous injection (iv).

The results showed that the blood concentration of Cosyntropin after the small-intestinal administration at 200 µg/kg was lower than the detection limit of ELISA. After addition of the composition of the present invention, the bioavailability of small-intestinal administration could reach 1.93%.

Example 16. The Composition of the Present Invention Significantly Improves Bioavailability of Octreotide after Small-Intestinal Administration The composition of the present invention: sodium lauryl sulfate, carbomer, chitosan, and sodium citrate, in a weight ratio of 21:7:6:69.

Octreotide and the composition of the present invention were mixed thoroughly in a weight ratio of 1:5, and reserved for further use.

Laboratory Animals: Adult Male SD Rats.

PK test for small-intestinal administration: Octreotide was administered to fasted adult SD rats in a volume of 1 ml/kg via a small-intestine catheter, such that the dose of Octreotide was 200 µg/kg. In another group, Octreotide at 200 µg/kg together with the composition of the present invention was injected via a small-intestine catheter (ei), and blood samples were collected from tail vein at 0 h, 0.5 h, 1 h, 1.5 h, 2 h, 2.5 h and 3 h after administration. The blood samples were anticoagulated with 10 mM EDTA and centrifuged at 4° C. at 3000 rpm for 5 min. The plasma was collected and subjected to quick freezing.

PK test for intravenous administration: Octreotide was intravenously injected to fasted animals at 1 µg/kg, and blood samples were collected at 5, 15, 30, 60, 90 and 120 min. The blood samples were anticoagulated with 10 mM EDTA and centrifuged at 4° C. at 3000 rpm for 5 min. The plasma was collected and subjected to quick freezing.

ELISA assay: Coating with a mouse monoclonal antibody against the target polypeptide, blocking with 1% BSA, incubating with a blood sample or a standard diluted with 0.1% BSA, capturing with Biotin-labeled rabbit polyclonal antibody against the target polypeptide, incubating with HRP-conjugated strepavidin, then developing with TMB, which was stopped with HCl, and reading at 450 nm. A standard curve was obtained from standards, and the concentration of the target polypeptide in the plasma was calculated.

AUC was calculated based on the PK curve, and the bioavailability of small-intestinal administration was calculated with respect to 100% of the bioavailability of intravenous injection (iv).

The results showed that the blood concentration of Octreotide after the small-intestinal administration at 200 µg/kg was lower than the detection limit of ELISA. After addition of the composition of the present invention, the bioavailability of small-intestinal administration could reach 1.71%.

Example 17. The Composition of the Present Invention Significantly Improves Bioavailability of Mecasermin after Small-Intestinal Administration The composition of the present invention: sodium lauryl sulfate, carbomer, chitosan, and sodium citrate, in a weight ratio of 21:6:7:65.

Mecasermin and the composition of the present invention were mixed thoroughly in a weight ratio of 1:5, and reserved for further use.

Laboratory Animals: Adult Male SD Rats.

PK test for small-intestinal administration: Mecasermin was administered to fasted adult SD rats in a volume of 1 ml/kg via a small-intestine catheter, such that the dose of Mecasermin was 200 µg/kg. In another group, Mecasermin at 200 µg/kg together with the composition of the present invention was injected via a small-intestine catheter (ei), and blood samples were collected from tail vein at 0 h, 0.5 h, 1 h, 1.5 h, 2 h, 2.5 h and 3 h after administration. The blood samples were anticoagulated with 10 mM EDTA and centrifuged at 4° C. at 3000 rpm for 5 min. The plasma was collected and subjected to quick freezing.

PK test for intravenous administration: Mecasermin was intravenously injected to fasted animals at 1 µg/kg, and blood samples were collected at 5, 15, 30, 60, 90 and 120 min. The blood samples were anticoagulated with 10 mM EDTA and centrifuged at 4° C. at 3000 rpm for 5 min. The plasma was collected and subjected to quick freezing.

ELISA assay: Coating with a mouse monoclonal antibody against the target polypeptide, blocking with 1% BSA, incubating with a blood sample or a standard diluted with 0.1% BSA, capturing with Biotin-labeled rabbit polyclonal antibody against the target polypeptide, incubating with HRP-conjugated strepavidin, then developing with TMB, which was stopped with HCl, and reading at 450 nm. A standard curve was obtained from standards, and the concentration of the target polypeptide in the plasma was calculated.

AUC was calculated based on the PK curve, and the bioavailability of small-intestinal administration was calculated with respect to 100% of the bioavailability of intravenous injection (iv).

The results showed that the blood concentration of Mecasermin after the small-intestinal administration at 200 μg/kg was lower than the detection limit of ELISA. After addition of the composition of the present invention, the bioavailability of small-intestinal administration could reach 1.38%.

Example 18. The Composition of the Present Invention Significantly Improves Bioavailability of Teriparatide after Small-Intestinal Administration The composition of the present invention: sodium lauryl sulfate, carbomer, chitosan, and sodium citrate, in a weight ratio of 20:6.5:6.5:65.

Teriparatide and the composition of the present invention were mixed thoroughly in a weight ratio of 1:5, and reserved for further use.

Laboratory Animals: Adult Male SD Rats.

PK test for small-intestinal administration: Teriparatide was administered to fasted adult SD rats in a volume of 1 ml/kg via a small-intestine catheter, such that the dose of Teriparatide was 200 μg/kg. In another group, Teriparatide at 200 μg/kg together with the composition of the present invention was injected via a small-intestine catheter (ei), and blood samples were collected from tail vein at 0 h, 0.5 h, 1 h, 1.5 h, 2 h, 2.5 h and 3 h after administration. The blood samples were anticoagulated with 10 mM EDTA and centrifuged at 4° C. at 3000 rpm for 5 min. The plasma was collected and subjected to quick freezing.

PK test for intravenous administration: Teriparatide was intravenously injected to fasted animals at 1 μg/kg, and blood samples were collected at 5, 15, 30, 60, 90 and 120 min. The blood samples were anticoagulated with 10 mM EDTA and centrifuged at 4° C. at 3000 rpm for 5 min. The plasma was collected and subjected to quick freezing.

ELISA assay: Coating with a mouse monoclonal antibody against the target polypeptide, blocking with 1% BSA, incubating with a blood sample or a standard diluted with 0.1% BSA, capturing with Biotin-labeled rabbit polyclonal antibody against the target polypeptide, incubating with HRP-conjugated strepavidin, then developing with TMB, which was stopped with HCl, and reading at 450 nm. A standard curve was obtained from standards, and the concentration of the target polypeptide in the plasma was calculated.

AUC was calculated based on the PK curve, and the bioavailability of small-intestinal administration was calculated with respect to 100% of the bioavailability of intravenous injection (iv).

The results showed that the blood concentration of Teriparatide after the small-intestinal administration at 200 μg/kg was lower than the detection limit of ELISA. After addition of the composition of the present invention, the bioavailability of small-intestinal administration could reach 2.08%.

Example 19. The Composition of the Present Invention Significantly Improves Bioavailability of ACTH (Corticotropin) after Small-Intestinal Administration The composition of the present invention: sodium lauryl sulfate, carbomer, chitosan, and sodium citrate, in a weight ratio of 20:6.5:6.5:65.

ACTH and the composition of the present invention were mixed thoroughly in a weight ratio of 1:5, and reserved for further use.

Laboratory Animals: Adult Male SD Rats.

PK test for small-intestinal administration: ACTH was administered to fasted adult SD rats in a volume of 1 ml/kg via a small-intestine catheter, such that the dose of ACTH was 200 μg/kg. In another group, ACTH at 200 μg/kg together with the composition of the present invention was injected via a small-intestine catheter (ei), and blood samples were collected from tail vein at 0 h, 0.5 h, 1 h, 1.5 h, 2 h, 2.5 h and 3 h after administration. The blood samples were anticoagulated with 10 mM EDTA and centrifuged at 4° C. at 3000 rpm for 5 min. The plasma was collected and subjected to quick freezing.

PK test for intravenous administration: ACTH was intravenously injected to fasted animals at 1 μg/kg, and blood samples were collected at 5, 15, 30, 60, 90 and 120 min. The blood samples were anticoagulated with 10 mM EDTA and centrifuged at 4° C. at 3000 rpm for 5 min. The plasma was collected and subjected to quick freezing.

ELISA assay: Coating with a mouse monoclonal antibody against the target polypeptide, blocking with 1% BSA, incubating with a blood sample or a standard diluted with 0.1% BSA, capturing with Biotin-labeled rabbit polyclonal antibody against the target polypeptide, incubating with HRP-conjugated strepavidin, then developing with TMB, which was stopped with HCl, and reading at 450 nm. A standard curve was obtained from standards, and the concentration of the target polypeptide in the plasma was calculated.

AUC was calculated based on the PK curve, and the bioavailability of small-intestinal administration was calculated with respect to 100% of the bioavailability of intravenous injection (iv).

The results showed that the blood concentration of ACTH after the small-intestinal administration at 200 μg/kg was lower than the detection limit of ELISA. After addition of the composition of the present invention, the bioavailability of small-intestinal administration could reach 1.86%.

Example 20. The Composition of the Present Invention Significantly Improves Bioavailability of Pramlintide after Small-Intestinal Administration The composition of the present invention: sodium lauryl sulfate, carbomer, chitosan, and sodium citrate, in a weight ratio of 20:6.5:6.5:65.

Pramlintide and the composition of the present invention were mixed thoroughly in a weight ratio of 1:5, and reserved for further use.

Laboratory Animals: Adult Male SD Rats.

PK test for small-intestinal administration: Pramlintide was administered to fasted adult SD rats in a volume of 1 ml/kg via a small-intestine catheter, such that the dose of Pramlintide was 200 μg/kg. In another group, Pramlintide at 200 μg/kg together with the composition of the present invention was injected via a small-intestine catheter (ei), and blood samples were collected from tail vein at 0 h, 0.5 h, 1 h, 1.5 h, 2 h, 2.5 h and 3 h after administration. The blood samples were anticoagulated with 10 mM EDTA and centrifuged at 4° C. at 3000 rpm for 5 min. The plasma was collected and subjected to quick freezing.

PK test for intravenous administration: Pramlintide was intravenously injected to fasted animals at 1 μg/kg, and blood samples were collected at 5, 15, 30, 60, 90 and 120 min. The blood samples were anticoagulated with 10 mM EDTA and centrifuged at 4° C. at 3000 rpm for 5 min. The plasma was collected and subjected to quick freezing.

ELISA assay: Coating with a mouse monoclonal antibody against the target polypeptide, blocking with 1% BSA, incubating with a blood sample or a standard diluted with 0.1% BSA, capturing with Biotin-labeled rabbit polyclonal antibody against the target polypeptide, incubating with HRP-conjugated strepavidin, then developing with TMB, which was stopped with HCl, and reading at 450 nm. A standard curve was obtained from standards, and the concentration of the target polypeptide in the plasma was calculated.

AUC was calculated based on the PK curve, and the bioavailability of small-intestinal administration was calculated with respect to 100% of the bioavailability of intravenous injection (iv).

The results showed that the blood concentration of Pramlintide after the small-intestinal administration at 200 μg/kg was lower than the detection limit of ELISA. After addition of the composition of the present invention, the bioavailability of small-intestinal administration could reach 1.77%.

Example 21. The Composition of the Present Invention Significantly Improves Bioavailability of Vapreotide after Small-Intestinal Administration The composition of the present invention: sodium lauryl sulfate, carbomer, chitosan, and sodium citrate, in a weight ratio of 20:6.5:6.5:65.

Vapreotide and the composition of the present invention were mixed thoroughly in a weight ratio of 1:5, and reserved for further use.

Laboratory Animals: Adult Male SD Rats.

PK test for small-intestinal administration: Vapreotide was administered to fasted adult SD rats in a volume of 1 ml/kg via a small-intestine catheter, such that the dose of Vapreotide was 200 μg/kg. In another group, Vapreotide at 200 μg/kg together with the composition of the present invention was injected via a small-intestine catheter (ei), and blood samples were collected from tail vein at 0 h, 0.5 h, 1 h, 1.5 h, 2 h, 2.5 h and 3 h after administration. The blood samples were anticoagulated with 10 mM EDTA and centrifuged at 4° C. at 3000 rpm for 5 min. The plasma was collected and subjected to quick freezing.

PK test for intravenous administration: Vapreotide was intravenously injected to fasted animals at 1 μg/kg, and blood samples were collected at 5, 15, 30, 60, 90 and 120 min. The blood samples were anticoagulated with 10 mM EDTA and centrifuged at 4° C. at 3000 rpm for 5 min. The plasma was collected and subjected to quick freezing.

ELISA assay: Coating with a mouse monoclonal antibody against the target polypeptide, blocking with 1% BSA, incubating with a blood sample or a standard diluted with 0.1% BSA, capturing with Biotin-labeled rabbit polyclonal antibody against the target polypeptide, incubating with HRP-conjugated strepavidin, then developing with TMB, which was stopped with HCl, and reading at 450 nm. A standard curve was obtained from standards, and the concentration of the target polypeptide in the plasma was calculated.

AUC was calculated based on the PK curve, and the bioavailability of small-intestinal administration was calculated with respect to 100% of the bioavailability of intravenous injection (iv).

The results showed that the blood concentration of Vapreotide after the small-intestinal administration at 200 μg/kg was lower than the detection limit of ELISA. After addition of the composition of the present invention, the bioavailability of small-intestinal administration could reach 1.69%.

Example 22. The Composition of the Present Invention Significantly Improves Bioavailability of Abaloparatide after Small-Intestinal Administration The composition of the present invention: sodium lauryl sulfate, carbomer, chitosan, and sodium citrate, in a weight ratio of 20:6.5:6.5:65.

Abaloparatide and the composition of the present invention were mixed thoroughly in a weight ratio of 1:5, and reserved for further use.

Laboratory Animals: Adult Male SD Rats.

PK test for small-intestinal administration: Abaloparatide was administered to fasted adult SD rats in a volume of 1 ml/kg via a small-intestine catheter, such that the dose of Abaloparatide was 200 μg/kg. In another group, Abaloparatide at 200 μg/kg together with the composition of the present invention was injected via a small-intestine catheter (ei), and blood samples were collected from tail vein at 0 h, 0.5 h, 1 h, 1.5 h, 2 h, 2.5 h and 3 h after administration. The blood samples were anticoagulated with 10 mM EDTA and centrifuged at 4° C. at 3000 rpm for 5 min. The plasma was collected and subjected to quick freezing.

PK test for intravenous administration: Abaloparatide was intravenously injected to fasted animals at 1 μg/kg, and blood samples were collected at 5, 15, 30, 60, 90 and 120 min. The blood samples were anticoagulated with 10 mM EDTA and centrifuged at 4° C. at 3000 rpm for 5 min. The plasma was collected and subjected to quick freezing.

ELISA assay: Coating with a mouse monoclonal antibody against the target polypeptide, blocking with 1% BSA, incubating with a blood sample or a standard diluted with 0.1% BSA, capturing with Biotin-labeled rabbit polyclonal antibody against the target polypeptide, incubating with HRP-conjugated strepavidin, then developing with TMB, which was stopped with HCl, and reading at 450 nm. A standard curve was obtained from standards, and the concentration of the target polypeptide in the plasma was calculated.

AUC was calculated based on the PK curve, and the bioavailability of small-intestinal administration was calculated with respect to 100% of the bioavailability of intravenous injection (iv).

The results showed that the blood concentration of Abaloparatide after the small-intestinal administration at 200 μg/kg was lower than the detection limit of ELISA. After addition of the composition of the present invention, the bioavailability of small-intestinal administration could reach 1.66%.

Example 23. The Composition of the Present Invention Significantly Improves Bioavailability of Growth Hormone (rhGH) after Small-Intestinal Administration The composition of the present invention: sodium lauryl sulfate, carbomer, chitosan, and sodium citrate, in a weight ratio of 20:6.5:6.5:65.

Growth Hormone and the composition of the present invention were mixed thoroughly in a weight ratio of 1:5, and reserved for further use.

Laboratory Animals: Adult Male SD Rats.

PK test for small-intestinal administration: Growth Hormone was administered to fasted adult SD rats in a volume of 1 ml/kg via a small-intestine catheter, such that the dose of Growth Hormone was 200 µg/kg. In another group, Growth Hormone at 200 µg/kg together with the composition of the present invention was injected via a small-intestine catheter (ei), and blood samples were collected from tail vein at 0 h, 0.5 h, 1 h, 1.5 h, 2 h, 2.5 h and 3 h after administration. The blood samples were anticoagulated with 10 mM EDTA and centrifuged at 4° C. at 3000 rpm for 5 min. The plasma was collected and subjected to quick freezing.

PK test for intravenous administration: Growth Hormone was intravenously injected to fasted animals at 1 µg/kg, and blood samples were collected at 5, 15, 30, 60, 90 and 120 min. The blood samples were anticoagulated with 10 mM EDTA and centrifuged at 4° C. at 3000 rpm for 5 min. The plasma was collected and subjected to quick freezing.

ELISA assay: Coating with a mouse monoclonal antibody against the target polypeptide, blocking with 1% BSA, incubating with a blood sample or a standard diluted with 0.1% BSA, capturing with Biotin-labeled rabbit polyclonal antibody against the target polypeptide, incubating with HRP-conjugated strepavidin, then developing with TMB, which was stopped with HCl, and reading at 450 nm. A standard curve was obtained from standards, and the concentration of the target polypeptide in the plasma was calculated.

AUC was calculated based on the PK curve, and the bioavailability of small-intestinal administration was calculated with respect to 100% of the bioavailability of intravenous injection (iv).

The results showed that the blood concentration of Growth Hormone after the small-intestinal administration at 200 µg/kg was lower than the detection limit of ELISA. After addition of the composition of the present invention, the bioavailability of small-intestinal administration could reach 0.32%.

Example 24. The Composition of the Present Invention Significantly Improves Bioavailability of Thymosin Alpha-1 after Small-Intestinal Administration The composition of the present invention: sodium lauryl sulfate, carbomer, chitosan, and sodium citrate, in a weight ratio of 20:6.5:6.5:65.

Thymosin alpha-1 and the composition of the present invention were mixed thoroughly in a weight ratio of 1:5, and reserved for further use.

Laboratory Animals: Adult Male SD Rats.

PK test for small-intestinal administration: Thymosin alpha-1 was administered to fasted adult SD rats in a volume of 1 ml/kg via a small-intestine catheter, such that the dose of Thymosin alpha-1 was 200 µg/kg. In another group, Thymosin alpha-1 at 200 µg/kg together with the composition of the present invention was injected via a small-intestine catheter (ei), and blood samples were collected from tail vein at 0 h, 0.5 h, 1 h, 1.5 h, 2 h, 2.5 h and 3 h after administration. The blood samples were anticoagulated with 10 mM EDTA and centrifuged at 4° C. at 3000 rpm for 5 min. The plasma was collected and subjected to quick freezing.

PK test for intravenous administration: Thymosin alpha-1 was intravenously injected to fasted animals at 1 µg/kg, and blood samples were collected at 5, 15, 30, 60, 90 and 120 min. The blood samples were anticoagulated with 10 mM EDTA and centrifuged at 4° C. at 3000 rpm for 5 min. The plasma was collected and subjected to quick freezing.

ELISA assay: Coating with a mouse monoclonal antibody against the target polypeptide, blocking with 1% BSA, incubating with a blood sample or a standard diluted with 0.1% BSA, capturing with Biotin-labeled rabbit polyclonal antibody against the target polypeptide, incubating with HRP-conjugated strepavidin, then developing with TMB, which was stopped with HCl, and reading at 450 nm. A standard curve was obtained from standards, and the concentration of the target polypeptide in the plasma was calculated.

AUC was calculated based on the PK curve, and the bioavailability of small-intestinal administration was calculated with respect to 100% of the bioavailability of intravenous injection (iv).

The results showed that the blood concentration of Thymosin alpha-1 after the small-intestinal administration at 200 µg/kg was lower than the detection limit of ELISA. After addition of the composition of the present invention, the bioavailability of small-intestinal administration could reach 0.65%.

Under the enlightenment of the specification, a person ordinarily skilled in the art can make many further embodiments that all fall within the scope of protection of the present invention, without departing from the scope of the claims of the present invention.

What is claimed is:

1. A composition for use in an oral formulation, comprising: a surfactant, an acrylic polymer, chitin or its derivatives, and a metal ion chelating agent; the surfactant, the acrylic polymer, the chitin or its derivatives, and the metal ion chelating agent are in a weight ratio of 15-25:5-8:5-8:50-80.

2. The composition according to claim 1, which is a pharmaceutical composition comprising: a surfactant, an acrylic polymer, chitin or its derivatives, and a metal ion chelating agent.

3. The composition according to claim 1, wherein the surfactant is one or more of anionic surfactants or nonionic surfactants.

4. The composition according to claim 1, wherein the acrylic polymer is one or more of carbomer, carbomer 910, carbomer 934, and carbomer 934P.

5. The composition according to claim 1, wherein the chitin or its derivatives is one or more of chitin, chitosan, carboxymethyl chitosan, acylated chitosan, alkylated chitosan, hydroxylated chitosan, quaternary ammonium chitosan, chitosan oligosaccharide, and chitosan sulfate.

6. The composition according to claim 1, wherein the metal ion chelating agent is one or more of citric acid and/or its salt, tartaric acid and/or its salt, malic acid and/or its salt, maleic acid and/or its salt, gluconic acid and/or its salt, ethylenediaminetetraacetic acid and/or its salt, aminotriacetic acid and/or its salt, and diethylenetriaminepentaacetic acid and/or its salt.

7. The composition according to claim 1, wherein the surfactant is sodium lauryl sulfate, the acrylic polymer is carbomer, the chitin or its derivatives are chitosan, and the metal ion chelating agent is sodium citrate.

8. The composition according to claim 1, wherein the surfactant, the acrylic polymer, the chitin or its derivatives, and the metal ion chelating agent are in a weight ratio of 19-21:6-7:6-7:60-70.

9. The composition according to claim 2, wherein a drug in the pharmaceutical composition is polypeptide, insulin, or growth hormone.

10. The composition according to claim 9, wherein the polypeptide includes: Exenatide, Nesiritide, Gonadorelin, Leuprolide, recombinant Glucagon, Oxytocin, Bivalirudin, Sermorelin, Gramicidin D, recombinant Insulin, Vasopressin, Cosyntropin, Octreotide, Vapreotide, Mecasermin, Teriparatide, ACTH, Pramlintide, Abaloparatide, rhGH, thymosin alpha-1.

11. The composition according to claim 2, wherein the drug and the composition comprising the surfactant, the acrylic polymer, the chitin or its derivatives, and the metal ion chelating agent are in a weight ratio of 1:5 in the pharmaceutical composition.

12. The composition according to claim 1, wherein the composition is prepared into an enteric capsule.

* * * * *